United States Patent [19]

Arthur et al.

[11] 4,314,969

[45] Feb. 9, 1982

[54] SUBMERSIBLE RESPIROMETER

[75] Inventors: Robert M. Arthur; Jerome J. Triatik, both of Fond du Lac, Wis.

[73] Assignee: Arthur Technology, Inc., Fond du Lac, Wis.

[21] Appl. No.: 182,664

[22] Filed: Aug. 29, 1980

[51] Int. Cl.³ .......................... C12K 1/34; G01N 7/00
[52] U.S. Cl. ........................................ 422/68; 73/19; 422/79; 435/291; 435/807
[58] Field of Search ................ 422/68, 79; 435/4, 34, 435/39, 291, 313, 807; 210/96.1, 614; 73/19

[56] References Cited

U.S. PATENT DOCUMENTS 3,731,522  5/1973  Mikesell ................................. 73/19
3,740,320  6/1973  Arthur ............................ 435/291 X
3,942,792  3/1976  Topol ................................... 73/19

Primary Examiner—Richard V. Fisher
Attorney, Agent, or Firm—Quarles & Brady

[57] ABSTRACT

A submersible recording respirometer includes an oxygen analyzer which measures the concentration of oxygen absorbed by a wastewater sample contained in an aeration chamber. The aeration chamber forms part of a housing which is submerged in the main body of wastewater and the aeration chamber is periodically drained, washed with fresh water and refilled with another wastewater sample. This cycle is accomplished automatically under the direction of a microprocessor-based control circuit which generates signals to a chart recorder that provides a hard copy of the measurement results.

10 Claims, 2 Drawing Figures 4,314,969

SUBMERSIBLE RESPIROMETER

BACKGROUND OF THE INVENTION

Biological activity of bacterial cultures has always been associated with gas production or gas utilization. Cellular metabolism, i.e., biological activity, in aerobic cultures is related to the utilization of oxygen and in anaerobic cultures to the production of methane. In water pollution, the food for the culture or organisms is waste matter and the quantity of oxygen utilized or methane produced indicates the amount of waste matter (food). The amount of food metabolized (or biological activity) is reflected in the rate of respiration or methane production. These rates are particularly useful to control wastewater treatment operations.

The most common method of measuring biological activity of wastewater is the 5-day B.O.D. (Biochemical Oxygen Demand). The 5-day B.O.D. is useful in describing the characteristics of plant influent or effluent and the oxygen demand on the stream, but it is useless for wastewater treatment control because of the five-day delay.

Another measurement which is used to indicate biological activity is to measure the change in volatile solids which is related to the amount of oxidizable material in the food. This measurement does not indicate the rate of respiration (i.e., metabolism) of the food.

Additional methods of measuring biological activity include chemical oxygen demand (C.O.D.), total organic carbon (T.O.C.) and other rapid combustion techniques. The results generally have little relationship to the measurement of respiration rates which is a relatively slow oxidation process that takes place under much different environmental conditions.

The actual biological activity of wastewater, i.e., respiration, is difficult to measure. Ideally, the rate should be measured without removing the sample from its environment. In the standard 5-day B.O.D. test, samples are incubated at average stream temperature (68 degrees, F.), seeded and buffered in an effort to simulate stream conditions.

In an attempt to produce a better indication of biological activity, especially in activated sludge waste treatment plants, dissolved oxygen probes have been placed in aeration tanks to give an indication of the oxygen utilized. At best, dissolved oxygen in a static measure of the concentration of oxygen at time t, but does not indicate the rate of oxygen demand. It the values of D.O. (Dissolved Oxygen) are plotted against time, the resulting graph indicates the rate of change of D.O., not oxygen demand. In effect, the graph is a measurement of the difference between the rate of demand and supply. If the rates are equal, the D.O. is constant, but the oxygen demand could be high. Oxygen demand rates can be used to predict changes in D.O. levels and are therefore particularly useful in control.

The apparatus and method of the instant invention can be used wherever it is necessary to monitor wastewater for information or control purposes. The rates of demand or production can be fed directly into recorders, data processors or controllers. Applications include:

Monitoring

Rivers, streams and lakes to determine the strength of pollution; industrial flows into sewer systems as a basis for sewer service fee; wastewater treatment plant effluents to report to regulatory agencies; determine plant efficiency by measuring oxygen demand of influent and effluent.

Process Control

Measure biological activity of activated sludge to control flow, aeration time or quantity of air; determine oxygen demand of effluents to control plant operation; measure oxygen demand of return sludge to control amount of return; measure rate of methane production in anaerobic digestors to control feeding and withdrawal cycles.

Respirometric methods of measuring biological activity date back to the early days of this century. Without this technique much of the present knowledge of cellular metabolism would be unknown.

Respirometry measures biological activity by relating changes in pressure in a closed system to oxygen demand. The pressure change is due to the volume decrease of gaseous oxygen during respiration, assuming any carbon dioxide produced in absorbed, as in a hydroxide solution. The term respirometry can also be applied to measuring the change of concentration of oxygen during respiration.

In prior U.S. Pat. No. 3,740,320 entitled "Apparatus and Method for Measuring the Amount of Gas Absorbed or Released by a Substance" there is described a recording respirometer which measures the rate of oxygen utilized by a respiring culture. When this apparatus is applied to measuring the biological activity of wastewater, for example, a sample of the water is placed in an aeration chamber and air is diffused through the sample. The oxygen content of this air is measured with an oxygen analyzer and recorded.

The accuracy of this prior recording respirometer depends on keeping the wastewater sample at the same temperature as the body of wastewater from which it was taken. To accomplish this in my prior structure, the aeration chamber is placed in a container and wastewater from the main body is circulated through the container to maintain the sample at the proper temperature. The pump, tubing and container add tremendously to the cost of the apparatus and they present added maintenance difficulties, particularly in winter.

SUMMARY OF THE INVENTION

The present invention relates to a submersible recording respirometer which includes a sensing unit to measure the change in concentration of a gas released or absorbed by a liquid, a submerged aeration chamber for containing a sample of the liquid and a system for periodically draining, washing and refilling the aeration chamber with a new sample. The aeration chamber is part of a housing which is submerged in the body of liquid to be measured and which also encloses equipment which cyclically allows liquid samples to enter the aeration chamber, measure the oxygen content of the samples for a preselected time interval, and then clean out the aeration chamber in preparation for the subsequent cycle.

A general object of the invention is to provide an accurate measurement of the rate of change of oxygen concentration in a body of wastewater. Accuracy is achieved by placing the measurement system in the main body of wastewater where the measurement is made at the proper temperature. Although air and electrical signals are supplied to the submerged housing, the pumping of liquids from the main body with the attendant cost is not required. The oxygen sensor may also be disposed in the submerged housing and an electrical signal indicating oxygen concentration is carried to the surface.

Another object of the invention is to provide a control circuit for operating the air pumps and solenoids during the measurement cycle. The control circuit is located in an enclosure above the liquid surface and it provides means for entering data which presets the cycle time and it displays information concerning the operation of the system.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
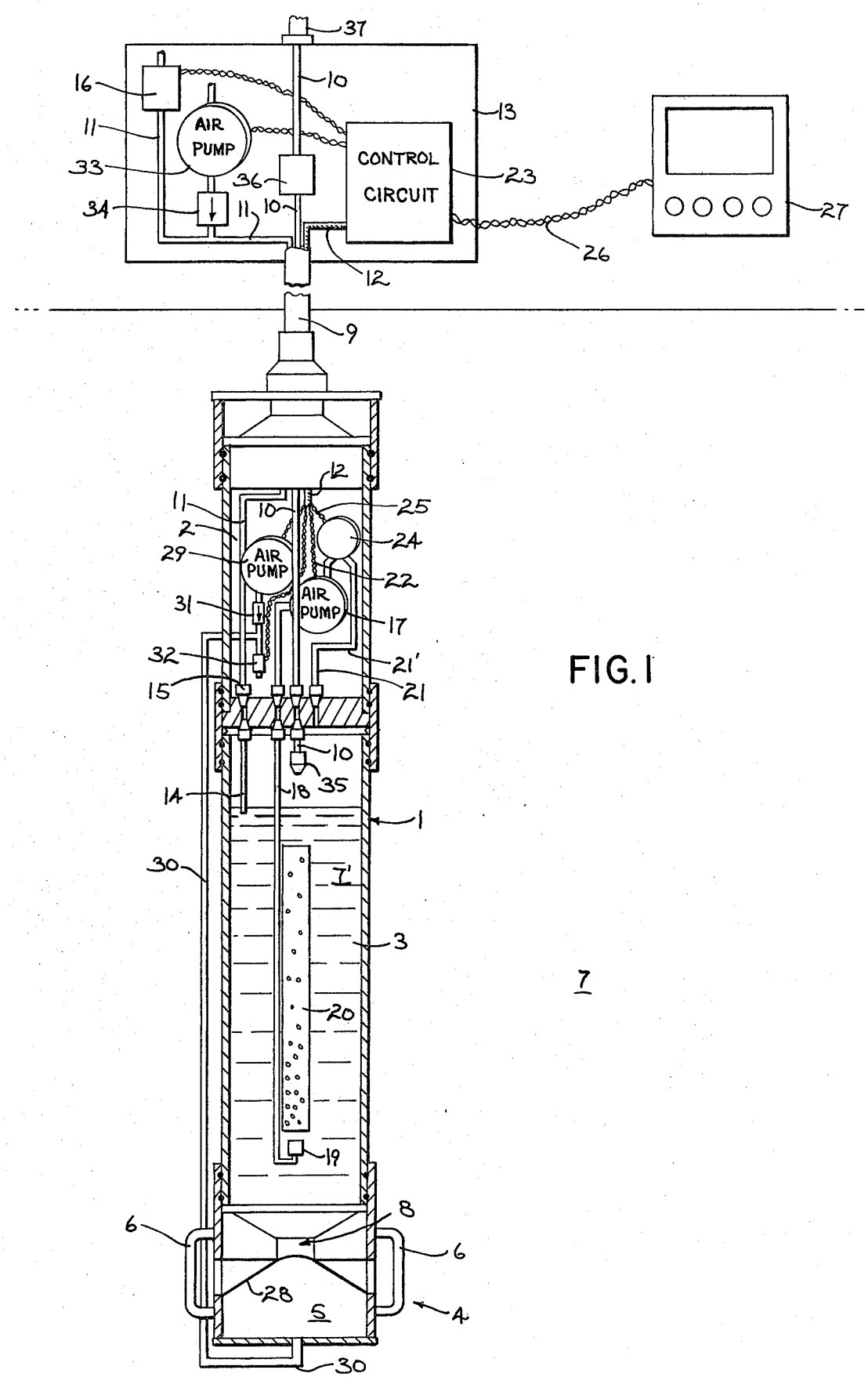
FIG. 1 is a view in cross section of the submersible respirometer of the present invention.

The preferred embodiment of the submersible respirometer is particularly suitable for use in a treatment plant where it is submerged in the wastewater. It includes a housing 1 which is generally cylindrical in shape and which is divided into three sections 2–4. The upper section 2 forms a watertight equipment chamber for a variety of pumps and valves to be described in detail hereinafter, the middle section 3 forms an aeration chamber, and the lower section 4 includes a diaphragm valve 5. The lower section of the housing 1 is attached to the middle section 3 by three stainless steel bars 6. An opening 8 is formed in the bottom of the aeration chamber 3 and it communicates with the lower section 4. As will be described in detail below, the diaphragm valve 5 controls the flow of liquid 7 through the opening 8 to enable liquid samples to enter the aeration chamber 3 and to enable the liquid samples to be flushed from the aeration chamber 3.

The housing 1 is held in place beneath the surface of the liquid 7 by a bracket (not shown) which is fabricated for the particular installation. A flexible conduit 9 fastens to the upper section 2 and it provides passage to the surface for a water line 10, an air line 11 and an electrical cable 12. Above the surface of the liquid 7 the conduit 9 connects to a control unit 13.

The aeration chamber 3 is periodically filled with a sample of the liquid 7 and the biological activity of this sample 7' is then measured. Filling of the aeration chamber 3 is accomplished by opening the diaphragm valve 5 and allowing liquid 7 to enter through the opening 8 at the bottom of the chamber 3. Filling continues until the sample level reaches the bottom of an air tube 14 which projects downward from the top of the middle chamber 3. The air tube 14 connects to the air line 11 at a connector 15 in the upper housing section 2 and the air line 11 is vented to atmospheric pressure by a solenoid valve 16 mounted in the control unit 13.

An air pump 17 mounted in the upper section 2 circulates the air trapped above the sample liquid 7'. An output line 18 on the air pump 17 extends downward through the sample liquid 7' and is terminated by a porous air diffuser 19. The air diffuser 19 is positioned directly beneath a circular cylindrical air lift column 20 which extends upward along the central axis of the aeration chamber 3. The intake side of the air pump 17 connects through a line 21 to a passage in the top of the aeration chamber 3, and it thus provides a return path for the air which is circulated through the sample liquid 7'. The operation of the air pump 17 is controlled through a pair of power lines 22 which electrically connect the air pump 17 to a control circuit 23 mounted in the control unit 13.

As air is circulated through the wastewater sample 7', oxygen is absorbed as a result of the biological activity in the sample. The amount of oxygen in the circulated air is continuously measured by an oxygen analyzer 24, which is mounted in the upper section 2 and which is connected to the air intake line 21. The oxygen analyzer 24 may be an oxygen probe such as those available commercially from Teledyne Inc. or a paramagnetic oxygen analyzer such as those available commercially from Servomex Chemical Instruments. It connects through wires 25 to the control circuit 23 which in turn connects through wires 26 to a chart recorder 27. The oxygen analyzer 24 is calibrated to indicate the concentration of oxygen in the air circulated through the wastewater sample 7' and it generates an electrical signal to the control circuit 23. The control circuit 23 generates a corresponding signal to the recorder 27 which prints a record of oxygen partial pressure as a function of time, or in other words, an oxygen consumption curve.

After the oxygen content of the wastewater sample 7' is measured for a preselected time interval, it is flushed from the aeration chamber 3. This occurs every fifteen to thirty minutes and is accomplished by opening the diaphragm valve 5 and forcing air into the chamber 3 through the air line 11 and air tube 14. When supplied with air under pressure, the valve's elastic membrane 28 expands upward to close the opening 8, and when vented to atmosphere, the membrane collapses to open the aeration chamber 3. Air pressure for the diaphragm valve 5 is provided by an air pump 29 which is mounted in the upper equipment section 2. The air pump 29 is connected to the valve 5 through a line 30 which extends down the outside of the housing 1. A check valve 31 is connected to the output of the air pump 29 and a solenoid valve 32 connects to the air line 30 to vent it to atmospheric pressure. Both the air pump 29 and the solenoid valve 32 electrically connect to the control circuit 23 through the cable 12 and they are sequentially operated to open and close the diaphragm valve 5 as each wastewater sample 7' is cycled through the system.

Pressurized air needed to expel the wastewater sample 7' from the aeration chamber 3 is provided by a third air pump 33 mounted in the control unit 13. It connects to the aeration chamber 3 through the air line 11 and a check valve 34 is connected in series with it to entrap air in the chamber 3 when the air pump 33 is not operating. As with the other electrically operable devices in the system, the air pump 33 is connected to the control circuit 23 and is turned on and off at the proper times in the sequence by the control circuit 23.

After the wastewater sample 7' is expelled from the aeration chamber 3 by operation of the air pump 33, the chamber 3 is flushed with clean water which enters through the water line 10. The water line 10 extends into the chamber 3 along its central axis and a nozzle 35 connects to its lower end. The water line 10 extends upward into the control unit 13 where it connects to a solenoid valve 36 which is electrically connected to the control circuit 23. Water under pressure is received through a pipe 37 and when the solenoid valve 36 is energized, clean water is sprayed from the nozzle 35 to flush out the inside of the aeration chamber 3. After flushing is completed, the solenoid valve 36 is deenergized and the solenoid valve 16 is energized to vent the aeration chamber 3 to atmospheric pressure. A new sample 7' is thus taken into the chamber 3 and the cycle repeats.

Figure 2:
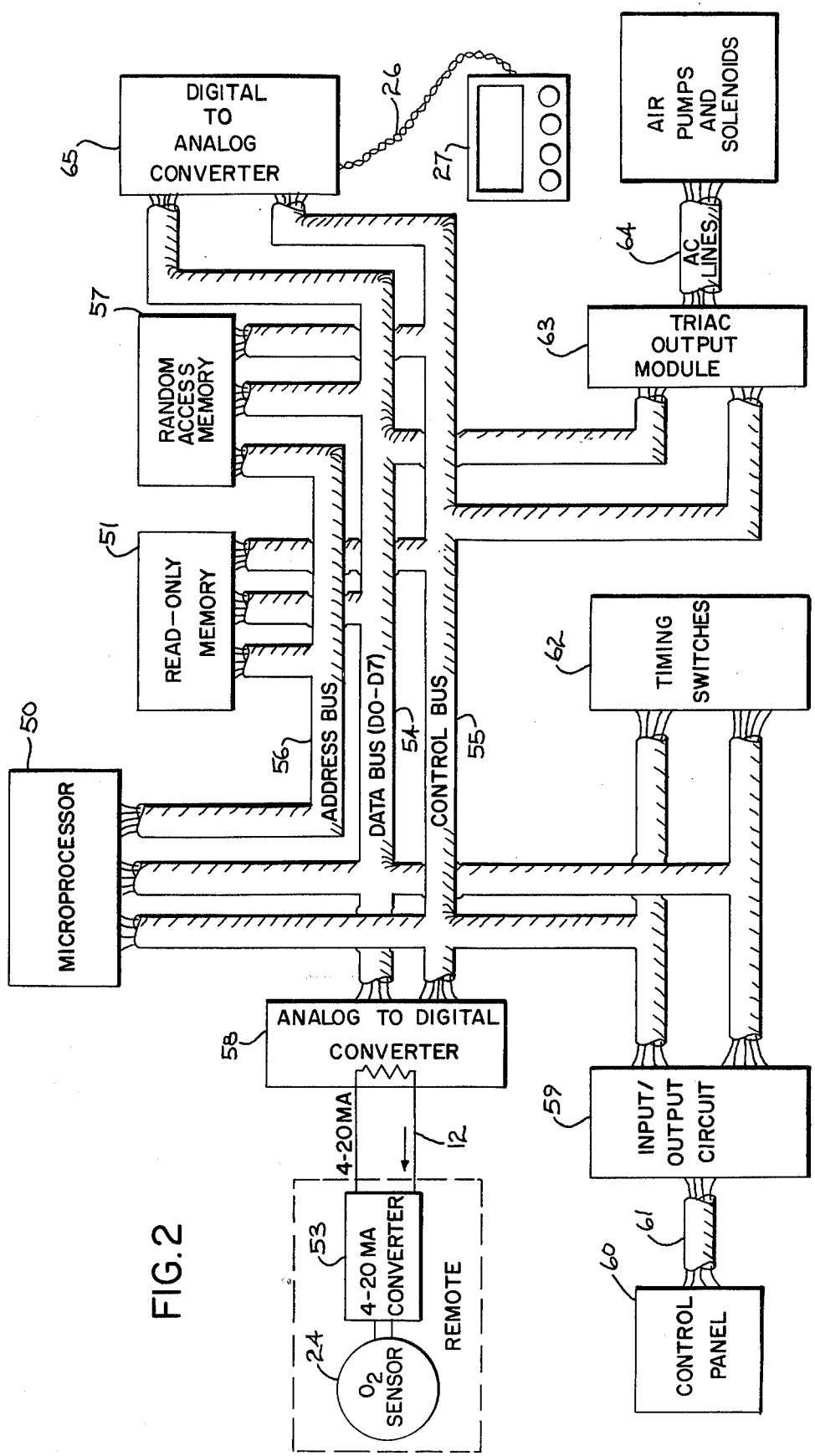
FIG. 2 is an electrical schematic diagram of the control circuit which forms part of the submersible respirometer of FIG. 1.

Referring particularly to FIG. 2, the control circuit 23 operates the pumps and solenoid valves of the submersible respirometer and it processes the signal received from the oxygen analyzer 24. The control circuit 23 includes an 8-bit microprocessor 50 and the functions it performs are determined by a control program which is stored in a read-only memory 51. The microprocessor 50 connects to the read-only memory 51 through an 8-bit data bus 54, an address bus 56 and a control bus 55. A static random access memory (RAM) 57 also connects to the microprocessor buses 54-56 and it provides temporary storage for intermediate results of calculations and buffer storage for input/output data.

The oxygen analyzer 24 is coupled to the control circuit 23 by a converter circuit 53 which amplifies its signal and generates a current ranging from four to twenty milliamperes. This current is applied to a 12-bit analog to digital converter circuit 58 wich connects to the microprocessor data bus 54 and control bus 55. In response to instructions in the control program, the microprocessor 50 periodically reads the 8-bit least significant byte output of the analog to digital converter 58 and the 4-bit most significant byte output and stores the resulting 12-bit oxygen concentration number in the RAM 57.

The oxygen concentration numbers input from the analog to digital converter 58 are employed to calculate a 12-bit oxygen partial pressure number which is output to a digital to analog converter circuit 65. The D/A circuit 65 connects to the microprocessor data bus 54 and control but 55, and periodically it is enabled to latch an 8-bit byte of data and a 4-bit byte of data which comprise the oxygen partial pressure number. This is converted to an analog electrical signal which is applied to the chart recorder to generate the oxygen consumption curve.

The microprocessor 50 operates uner the direction of the control program to sequentially operate the pumps and solenoid valves on the submersible respirometer. These output devices are coupled to the control circuit 23 through lines 64 that connect to a triac output module 63. The triac output module 63 connects to the microprocessor data but 54 and control bus 55, and it includes a set of triac circuits which are each connected to operate one of the pumps or solenoid valves in response to the logic state of the data bus. The operation of the pumps and solenoid valves is thus controlled by the microprocessor 50.

The timing of the various steps in the respirometer measurement cycle is determined by the control program, but may be manually preset. This is accomplished by a set of timing switches 62 that are coupled to the microprocessor data bus 54 and control bus 55. When the system is initialized during start-up, these switch settings are read and stored in the RAM 57 where they are employed in combination with a real-time clock to time the various steps in the measurement cycle.

The control circuit 23 is operated from a control panel 60 which connects to an I/O module 59 through a cable 61. The I/O module 59 is connected to the microprocessor data bus 54 and control bus 55, and the settings of the various control panel switches can be read and the control panel display can be energized under the direction of the control program.

It should be apparent that the microprocessor-based control circuit 23 allows a great deal of flexibility, due in large part because all functions may be altered merely by changing the control program. This enables the submersible respirometer to be employed with a variety of sensors and recording devices under many different operating conditions.

I claim:

1. A submersible respirometer, the combination comprising: a housing suitable for submersion in a body of liquid;
an aeration chamber formed within the housing and including an opening which communicates with the body of liquid in which the housing is submerged;
valve means mounted to said housing and being operable to open and close said opening to enable liquid samples to flow into and out of the aeration chamber;
an air circulation system for circulating air trapped within the aeration chamber above the liquid sample, said air circulation system including an air pump, an output line which connects to said air pump and extends beneath the surface of the liquid sample, and an intake line which connects to the air pump and communicates with the air space trapped within the aeration chamber above the liquid sample;
an oxygen analyzer operable to generate an electrical signal indicative of the amount of oxygen contained within the air trapped within the aeration chamber; and
means coupled to said aeration chamber for injecting pressurized air into it to expel the liquid sample from the aeration chamber through said opening.

2. The submersible respirometer as recited in claim 1 in which there is means for injecting fresh water into said aeration chamber that includes a waterline, which extends from the housing to above the surface of the body of liquid, and a valve which is operable to enable pressurized water to flow through said waterline into the aeration chamber.

3. The submersible respirometer as recited in claim 1 in which said means for injecting pressurized air into said aeration chamber includes an air tube which terminates inside the aeration chamber at a point below its upper surface such that it determines the amount of air entrapped in the aeration chamber when the aeration chamber is filled with a wastewater sample.

4. The submersible respirometer as recited in claim 1 in which said opening is located in the bottom of said aeration chamber.

5. The submersible respirometer as recited in claim 4 in which said valve means is a diaphragm valve mounted beneath said opening.

6. The submersible respirometer as recited in claim 1 in which said valve means, air circulation system and air injecting means are operated by a control circuit which includes a microprocessor that operates in response to a control program to continuously cycle liquid samples into said aeration chamber for measurement.

7. A submersible respirometer, the combination comprising: a housing suitable for submersion in a body of liquid;

an aeration chamber formed within the housing and including an opening which communicates with the body of liquid in which the housing is submerged;

valve means mounted to said housing and being operable to open and close said opening to enable liquid samples to flow into and out of the aeration chamber;

an air circulation system for circulating air trapped within the aeration chamber above the liquid sample, said air circulation system including an air pump mounted within said housing, an output line which connects to said air pump and extends beneath the surface of the liquid sample, and an intake line which connects to the air pump and communicates with the air space trapped within the aeration chamber above the liquid sample;

an oxygen analyzer mounted within said housing and operable to generate an electrical signal indicative of the amount of oxygen contained within the air trapped within the aeration chamber;

means coupled to said aeration chamber for injecting pressurized air into it to expel the liquid sample from the aeration chamber through said opening; and means connected to said housing for conveying air from above the surface of the liquid body to said housing and for coupling the electrical signal generated by said oxygen analyzer from the housing to a signal processor above the surface of the body of liquid.

8. The submersible respirometer as recited in claim 7 in which there is means for injecting fresh water into said aeration chamber that includes a waterline, which extends from the housing to above the surface of the body of liquid, and a valve which is operable to enable pressurized water to flow through said waterline into the aeration chamber.

9. The submersible respirometer as recited in claim 7 in which said means for injecting pressurized air into said aeration chamber includes an air tube which terminates inside the aeration chamber at a point below its upper surface such that it determines the amount of air entrapped in the aeration chamber when the aeration chamber is filled with a wastewater sample.

10. The submersible respirometer as recited in claim 7 in which said opening is located in the bottom of said aeration chamber and said valve means is mounted beneath said opening.

* * * * *